United States Patent [19]
Lee et al.

[11] Patent Number: 5,869,477
[45] Date of Patent: Feb. 9, 1999

[54] β-METHYLCARBAPENEM DERIVATIVES, PROCESS FOR THE PREPARATION THEREOF AND PHARMACEUTICAL COMPOSITION COMPRISING SAME

[75] Inventors: Cheol-Hae Lee, Daejeon; Dong-Ha Lee; Kyung-Sook Kim, both of Pusan; Jae-Hak Kim; Young-Sook Kim, both of Daejeon; Yu-Sung Jun, Youngdong-gun; Sung-Su Lim, Seongnam; Eun-Mi Bae; Bong-Jin Kim, both of Daejeon, all of Rep. of Korea

[73] Assignee: Korea Research Institute of Chemistry Technology, Daejeon, Rep. of Korea

[21] Appl. No.: 760,431

[22] Filed: Dec. 4, 1996

[30] Foreign Application Priority Data

Dec. 4, 1995 [KR] Rep. of Korea ............... 1995-46454

[51] Int. Cl.$^6$ ............... C07D 477/14; A61K 31/40
[52] U.S. Cl. ............... 514/210; 540/302
[58] Field of Search ............... 540/302; 514/210

[56] References Cited

U.S. PATENT DOCUMENTS

| | | |
|---|---|---|
| 4,429,128 | 1/1984 | Rosati ............... 540/302 |
| 4,479,947 | 10/1984 | Christensen ............... 514/99 |
| 5,064,954 | 11/1991 | Uyeo et al. ............... 540/302 |

OTHER PUBLICATIONS

Schmitt, S.M. et al. *Journal of Antibiotics*, vol. 41, pp. 780–787 (1988).

Bungaard, H. *Design of Prodrugs* (Elsevier, Amsterdam), edited by Bungaard, H., pp. 1–6 (1985).

*Primary Examiner*—Mark L. Berch
*Attorney, Agent, or Firm*—Anderson, Kill & Olick, P.C.

[57] ABSTRACT

A β-methylcarbapenem compound of formula (I), a salt or an ester thereof, a process for the preparation thereof and a anti-bacterial composition containing same:

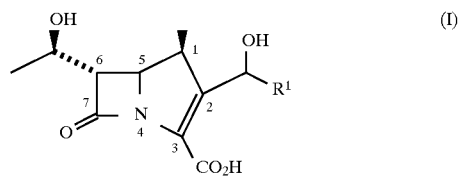

wherein:

$R^1$ is a $C_{1-6}$ alkyl, $C_{2-6}$ alkenyl, cycloalkyl, aryl or heterocyclic aryl group.

7 Claims, No Drawings

β-METHYLCARBAPENEM DERIVATIVES, PROCESS FOR THE PREPARATION THEREOF AND PHARMACEUTICAL COMPOSITION COMPRISING SAME

FIELD OF THE INVENTION

The present invention relates to β-methylcarbapenem derivatives which have excellent antibacterial activities against Gram-positive and Gram-negative bacteria excluding *Pseudomonas aeruginosa*, processes for the preparation thereof and pharmaceutical composition comprising same.

BACKGROUND OF THE INVENTION

Since thienamycin having a broad antibacterial spectrum was disclosed in U.S. Pat. No. 3,950,357, there have been many attempts to develop an even more active antibiotic which is stable against the attack of dehydropeptidase-I.

For instance, European Patent No. 126587 reports *meropenem* and Japanese Patent No. 425779 presents *biapenem*, for use in injection formulations. Recently, European Patent No. 416953 have disclosed *tribactam* compounds, which are carbapenem antibiotics suitable for oral administration.

However, the above carbapenem antibiotics have a problem in that the process of isolating the intended isomer is complicated, requiring more than 12 steps. Further, they show low antibacterial activities against *Streptococcus facium* and *Enterobacter cloacae*, and no activity against *Pseudomonas aeruginosa*.

Therefore, there has been a need to develop an antibiotic having an improved antibacterial activity against Gram-positive and Gram-negative bacteria.

SUMMARY OF THE INVENTION

Accordingly, it is an object of the present invention to provide a carbapenem derivative which has an enhanced antibacterial activity against Gram-positive and -negative bacteria.

Another object of the present invention is to provide a process for preparing said carbapenem derivative.

A further object of the present invention is to provide a pharmaceutical composition comprising said carbapenem derivative as an active ingredient.

In accordance with one aspect of the present invention, there is provided a B-methylcarbapenem derivative of formula (I), a salt or an ester thereof:

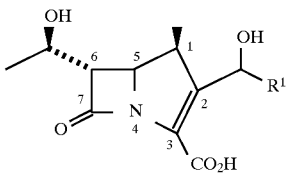

wherein:
R$^1$ is a C$_{1-6}$ alkyl, C$_{2-6}$ alkenyl, cycloalkyl, aryl or thiazolyl group.

DETAILED DESCRIPTION OF THE INVENTION

The β-methylcarbapenem compound of formula (I) or its derivative may have a plurality of chiral carbons, and therefore, it is inclusive of all possible stereoisomers, e.g., an optically pure single isomer, a racemic mixture, and a diastereomeric mixture. For instance, the β-methylcarbapenem compound of formula (I) may include the stereoisomer of formula (Ia) or (Ib), or a mixture thereof:

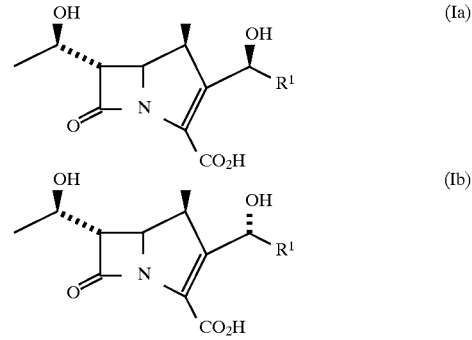

In accordance with one aspect of the present invention, R$^1$ is preferably an isopropyl, cyclopropyl, cyclopentyl or thiazolyl group. The preferred salt of the compound of formula (I) is of Na, K, Ca, lysine, ethanolamine or N,N'-dibenzylethyleneamine, wherein Na and K are most preferred; and the preferred ester of the compound of formula (I) is an ester obtained by replacing the carboxyl group with —CO$_2$R$^4$, R$^4$ being 5-methyldioxolenonemethyl, pivaloyloxymethyl, cyclohexyloxycarbonyloxyethyl or isopropyloxycarbonyloxyethyl.

Examples of the most desirable compounds of formula (I) according to the present invention are:

(1S, 5R, 6S)-2-[(1R)-1-hydroxy-2-methylpropyl]-6-[(1R)-1-hydroxyethyl]-1-methyl-2-carbapenem-3-carboxylic acid;

(1S, 5R, 6S)-2-[(1S)-1-hydroxy-2-methylpropyl]-6-[(1R)-1-hydroxyethyl]-1-methyl-2-carbapenem-3-carboxylic acid;

(1S, 5R, 6S)-2-[(R)-(cyclopropyl)hydroxymethyl]-6-[(1R)-1-hydroxyethyl]-1-methyl-2-carbapenem-3-carboxylic acid;

(1S, 5R, 6S)-2-[(S)-(cyclopropyl)hydroxymethyl]-6-[(1R)-1-hydroxyethyl]-1-methyl-2-carbapenem-3-carboxylic acid;

(1S, 5R, 6S)-2-[(R)-(cyclopentyl)hydroxymethyl]-6-[(1R)-1-hydroxyethyl]-1-methyl-2-carbapenem-3-carboxylic acid;

(1S, 5R, 6S)-2-[(S)-(cyclopentyl)hydroxymethyl]-6-[(1R)-1-hydroxyethyl]-1-methyl-2-carbapenem-3-carboxylic acid;

(1S, 5R, 6S)-2-[(R)-(1,3-thiazolyl)hydroxymethyl]-6-[(1R)-1-hydroxyethyl]-1-methyl-2-carbapenem-3-carboxylic acid;

(1S, 5R, 6S)-2-[(S)-(1,3-thiazolyl)hyl]-6-[(1R)-1-hydroxyethyl]-1-methyl-2-carbapenem-3-carboxylic acid;

(1S, 5R, 6S)-2-[(1R)-1-hydroxy-2,2-dimethylpropyl]-6-[(1R)-1-hydroxyethyl]-1-methyl-2-carbapenem-3-carboxylic acid;

(1S, 5R, 6S)-2-[(1S)-1-hydroxy-2,2-dimethylpropyl]-6-[(1R)-1-hydroxyethyl]-1-methyl-2-carbapenem-3-carboxylic acid;

(1S, 5R, 6S)-2-[(1R)-1-hydroxy-3-methylbutyl]-6-[(1R)-1-hydroxyethyl]-1-methyl-2-carbapenem-3-carboxylic acid;

(1S, 5R, 6S)-2-[(1S)-1-hydroxy-3-methylbutyl]-6-[(1R)-1-hydroxyethyl]-1-methyl-2-carbapenem-3-carboxylic acid;

(1S, 5R, 6S)-2-[(1R)-1-hydroxy-3-buten-1-yl]-6-[(1R)-1-hydroxyethyl]-1-methyl-2-carbapenem-3-carboxylic acid;

(1S, 5R, 6S)-2-[(1S)-1-hydroxy-3-buten-1-yl]-6-[(1R)-1-hydroxyethyl]-1-methyl-2-carbapenem-3-carboxylic acid;

(1S, 5R, 6S)-2-[(R)-(phenyl)hydroxymethyl]-6-[(1R)-1-hydroxyethyl]-1-methyl-2-carbapenem-3-carboxylic acid; and (1S, 5R, 6S)-2-[(S)-(phenyl)hydroxymethyl]-6-[(1R)-1-hydroxyethyl]-1-methyl-2-carbapenem-3-carboxylic acid.

Examples of the most desirable esters of the β-methylcarbapenem compound of formula (I) according to the present invention are:

(5-Methyl-2-oxo-1,3-dioxolen-4-yl)methyl (1S, 5R, 6S)-2-[(R)-(cyclopropyl)hydroxymethyl]-6-[(1R)-1-hydroxyethyl]-1-methyl-2-carbapenem-3-carboxylate;

(5-Methyl-2-oxo-1,3-dioxolen-4-yl)methyl (1S, 5R, 6S)-2-[(R)-(cyclopentyl)hydroxymethyl]-6-[(1R)-1-hydroxyethyl]-1-methyl-2-carbapenem-3-carboxylate;

(5-Methyl-2-oxo-1,3-dioxolen-4-yl)methyl (1S, 5R, 6S)-2-[(1R)-1-hydroxy-2-methylpropyl]-6-[(1R)-1-hydroxyethyl]-1-methyl-2-carbapenem-3-carboxylate;

Cyclohexyloxycarbonyloxy-1-ethyl (1S, 5R, 6S)-2-[(1R)-1-hydroxy-2-methylpropyl]-6-[(1R)-1-hydroxyethyl]-1-methyl-2-carbapenem-3-carboxylate;

Isopropyloxycarbonyloxy-1-ethyl (1S, 5R, 6S)-2-[(1R)-1-hydroxy-2-methylpropyl]-6-[(1R)-1-hydroxyethyl]-1-methyl-2-carbapenem-3-carboxylate; and Pivaloyloxymethyl (1S, 5R, 6S)-2-[(1R)-1-hydroxy-2-methylpropyl]-6-[(1R)-1-hydroxyethyl]-1-methyl-2-carbapenem-3-carboxylate.

The β-methylcarbapenems of formula (I) of the present invention may be prepared as in Scheme 1.

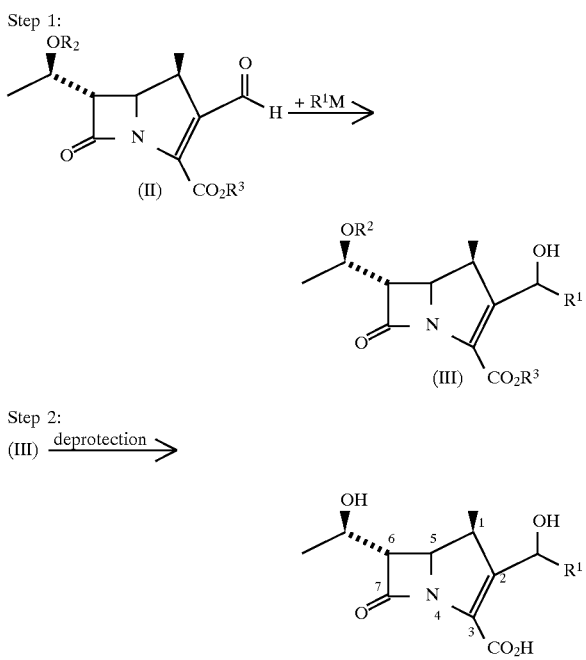

wherein:
$R^1$ has the same meaning as defined previously,
$R^2$ is a hydroxyl protecting group;
$R^3$ is a carboxyl protecting group; and
M is a metal atom.

Exemplary hydroxyl protecting groups that may be used in compounds (II) and (III) include trimethylsilyl, triethylsilyl, t-butyldimethylsilyl or allyloxycarbonyl group, wherein triethylsilyl or t-butyldimethylsilyl is more preferred.

Representative carboxyl protecting groups that may be used in compounds (II) and (III) include allyl, p-nitrophenyl, p-methoxybenzyl or p-t-butylbenzyl.

Suitable metal atoms useful in Step 1 include Mg or Li.

The preparation processes of Scheme 1 are illustrated as follows.

Step 1

Formyl carbapenem of formula (II) is reacted with $R^1M$ in a suitable solvent, e.g., diethylether, tetrahydrofuran (THF), and a mixture thereof to obtain a secondary alcohol of formula (III). The reaction may be carried out at a temperature ranging from −78° C. to room temperature for a period ranging from 5 min. to 2 hours.

The compound of formula (III) is obtained as a mixture of R and S isomers due to the newly-formed chiral carbon atom, and therefore, it may be desirable to separate the isomers, e.g., by a chromatographic separation, before subjecting the compound of formula (III) to Step 2.

Step 2

In Step 2, the hydroxyl and carboxyl protecting groups, i.e., $R^2$ and $R^3$, are removed from the compound of formula (III). The removal of the protecting groups may be carried out in accordance with known methods in the β-lactam chemistry.

For instance, when the hydroxyl protecting group, $R^2$, is a trimethylsilyl group, it may be removed by using 1M HCl, preferably in a mixture of THF and water at about 0° C. for a period ranging from 1 to 2 hours. When the reaction is completed, the desired product may be recovered and purified in accordance with a conventional method. The product is then subjected to a reaction to remove the carboxyl protecting group.

In case that the carboxyl protecting group, $R^3$, is a p-nitrobenzyl or p-t-butylbenzyl group, it may be removed by a catalytic reduction using a conventional catalyst, e.g., Pd/C and PtO, to obtain the desired products of formula (I). In case that $R^3$ is an allyl group, it may be removed by the reaction with tetrakis(triphenylphosphine)palladium(0), triphenylphosphine and 2-ethyl hexanoate in a suitable solvent, e.g., THF and methylene chloride, to obtain the desired products of formula (I).

The removal of carboxyl protecting group is preferably carried out at a temperature ranging from 15° to 30° C. for a period ranging from 2 to 3 hours.

The resulting compound of formula (I) may be separated into respective isomer of formula (Ia) and (Ib) in accordance with a conventional method, e.g., column chromatography. The structures of the two isomers thus separated are determined by the Mosher's method(Kakisawa, H., *J. Am. Chem. Soc.*, 113, 4092(1991)). The more polar isomer is identified as the R isomer, i.e., the compound of formula (Ib), and the less polar compound is the S isomer of formula (Ia).

The compound of formula (Ia) or (Ib) may be further converted into a pharmaceutically acceptable salt, e.g., a sodium or potassium salt.

On the other hand, an ester of the carbapenem of formula (I) of the present invention may be prepared as in Scheme 2.

Scheme 2

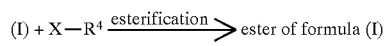

wherein:
$R^4$ is a pivaloyloxyalkyl, alkoxycarbonyloxyalkyl or alkyldioxolenonealkyl group; and
X is halogen or a sulfonate group.

In Scheme 2, the β-methylcarbapenem compound of formula (Ia) or (Ib) is esterified using $R^4X$, wherein X is Cl, Br, I, or a sulfonate group, e.g., methanesulfonate and p-toluenesulfonate.

The esterification may be carried out in an inert solvent in the presence of a base, at a temperature ranging from 0° to 25° C. for a period ranging from 0.5 to 3 hours. Examples of the inert solvent for the esterification include N,N-dimethylformamide, N,N-dimethylacetamide, dimethylsulfoxide, acetone, acetonitrile, methylethylketone and N-methylpyrrolidone. Representative bases that may be used in the esterification include inorganic bases such as sodium hydrogencarbonate, potassium carbonate, sodium carbonate and calcium carbonate, and organic bases such as triethylamine, dicyclohexylamine, diisopropylamine, N,N-dimethylaniline and 1,8-diazabicyclo[5.4.0]-undec-7-ene (DBU).

The β-methylcarbapenem compound of formula (I) and its derivatives of the present invention may be used for the treatment of topical or systemic infection of pathogenic bacteria in animals inclusive of human, due to their antibacterial activity. Therefore, the present invention also provides a pharmaceutical composition comprising the β-methylcarbapenem derivative of the present invention as an active ingredient, in combination with a pharmaceutically acceptable carrier or excipient. The pharmaceutical composition of the present invention may be administered orally or parenterally.

The daily dose of the β-methylcarbapenem derivative of the present invention may range from 2.5 to 100 mg/kg body weight, preferably, 5 to 60 mg/kg body weight, and they may be administered in a single dose or divided doses. However, the dosage may be adjusted based on all relevant factors, e.g., the patient's weight, age, sex, health condition and diet; the kind and severity of the disease; the type of formulation; excretion rate, mixing with other medicines; the compound used; the administration method thereof and others.

The following Examples are intended to further illustrate the present invention without limiting its scope.

Further, percentages given below for solid in solid mixture, liquid in liquid, and solid in liquid are on a wt/wt, vol/vol and wt/vol basis, respectively, unless specifically indicated otherwise.

Preparation Example 1
Preparation of allyl (1S, 5R, 6S)-2-formyl-6-[(1R)-1-triethylsilyloxyethyl]-1-methyl-2-carbapenem-3-carboxylate
(Method A)

10 g of allyl (1S, 5R, 6S)-2-hydroxymethyl-6-[(1R)-1-triethylsilyloxyethyl]-1-methyl-2-carbapenem-3-carboxylate was dissolved in 200 ml of dry dichloromethane at room temperature, and 33 g of manganese dioxide was added to the mixture. The resulting mixture was stirred at room temperature for 30 min., and then refluxed for 15 hours. The resulting reaction product was filtered through silica gel and Celite®, and the solvent was evaporated under a reduced pressure to obtain 8.2 g of the title compound.
(Method B)

To a mixture of 5.0 ml of dimethyl sulfoxide and 60 ml of dry dichloromethane, 5.5 ml of dry trifluoroacetic anhydride was added dropwise at −78° C., and stirred at −78° C. for 30 min. Added to the resulting mixture was a solution prepared by dissolving 5.0 g of (1S, 5R, 6S)-2-hydroxymethyl-6-[(1R)-1-triethylsilyloxyethyl]-1-methyl-2-carbapenem-3-carboxylate in 15 ml of dry dichloromethane, followed by adding 13.5 ml of triethylamine thereto. The resulting mixture was stirred at −78° C. for 1 hour, diluted with 20 ml of water, and then extracted with 60 ml of methylene chloride. The extract was washed successively with 1N HCl and a saturated sodium bicarbonate solution, and then dried over anhydrous magnesium sulfate. The solvent was removed by evaporation under a reduced pressure and the residue was subjected to column chromatography using a hexane/ethyl acetate eluent to obtain 3.1 g of the title compound.
$^1$ H NMR(CDCl$_3$) δ(ppm)
0.59(q, 8.0 Hz, 6 H), 0.93(t, J=8.0 Hz, 9 H), 1.21(d, J=6.2 Hz, 3 H), 1.25(d, 7.2 Hz, 3 H), 3.32–3.36(m, 1 H), 3.45(dd, J=7.2, 10.2 Hz, 1 H), 4.21–4.24(m, 1 H), 4.23(dd, J=3.5, 10.2 Hz, 1 H), 4.70–4.90(m, 2 H), 5.29(dd, J=1.4, 10.3 Hz, 1 H), 5.44(dd, J=1.4, 17.2 Hz, 1 H), 5.85–6.00(m, 1 H), 10.32(s, 1 H).

Preparation Example 2
Preparation of allyl (1S, 5R, 6S)-2-formyl-6-[(1R)-1-(diethyl-t-butylsilyloxy)ethyl]-1-methyl-2-carbapenem-3-carboxylate The procedure of the (Method A) of Preparation Example 1 was repeated except that 10 g of allyl (1S, 5R, 6S)-2-hydroxymethyl-6-[(1R)-1-diethyl-t-butylsilyloxyethyl]-1-methyl-2-carbapenem-3-carboxylate was employed as a starting material to obtain 8.2 g of the title compound.
$^1$ H NMR(CDCl$_3$) δ(ppm)
0.05(s, 6 H), 0.08(s, 9 H), 1.20(d, J=6.9 Hz, 6 H), 3.30–3.40 (m, 1 H), 3.45(dd, J=7.2, 10.2 Hz, 1 H), 4.21–4.24 (m, 1 H), 4.23(dd, J=3.5, 10.2 Hz, 1 H), 4.70–4.90(m, 2 H), 5.29(dd, J=1.4, 10.3 Hz, 1 H), 5.44(dd, J=1.4, 17.2 Hz, 1 H), 5.85(m, 1 H), 10.32(s, 1 H).

Example 1
Preparation of potassium (1S, 5R, 6S)-2-[(1R)-1-hydroxy-2-methylpropyl]-6-[(1R)-1-hydroxyethyl]-1-methyl-2-carbapenem-3-carboxylate
(Step 1)
Preparation of allyl (1S, 5R, 6S)-2-[(1R)-1-hydroxy-2-methylpropyl]-6-[(1R)-1-triethylsilyloxyethyl]-1-methyl-2-carbapenem-3-carboxylate 0.14 g of allyl (1S, 5R, 6S)-2-formyl-6-[(1R)-1-triethylsilyloxyethyl]-1-methyl-2-carbapenem-3-carboxylate prepared in Preparation Example 1 was dissolved in 5 ml of dry THF, and then the reaction vessel was cooled to −78° C. To the mixture was added 0.18 ml of 2M isopropyl magnesium chloride and the resulting mixture was stirred at −78° C. for 15 min. The reaction was terminated by adding an aqueous saturated ammonium chloride solution and the mixture was diluted with 40 ml of ethyl acetate. The organic layer was washed successively with water and an aqueous saturated sodium chloride solution, and then dried over anhydrous magnesium sulfate. The solvent was removed by evaporation and the residue was purified with a column chromatography to obtain 0.11 g of the title compound.
$^1$ H NMR(CDCl$_3$) δ(ppm)
0.57(q, J=8.0 Hz, 6 H), 0.82(d, J=6.7 Hz, 3 H), 0.92(t, J=8.0 Hz, 9 H), 1.02(d, J=6.7 Hz, 3 H), 1.22(d, J=6.2 Hz, 3 H), 1.24(d, J=7.3 Hz, 3 H), 1.80–2.06(m, 1 H), 2.46(d, J=5.0 Hz, 1 H), 3.08–3.13(m, 1 H), 3.18(dd, J=2.8, 6.5 Hz, 1 H), 4.08(dd, J=2.8, 10.0 Hz, 1 H), 4.12–4.22(m, 1 H), 4.58–4.76 (m, 3 H), 5.23(dd, J=1.4, 10.3 Hz, 1 H), 5.43(dd, J=1.4, 17.2 Hz, 1 H), 5.83–6.03(m, 1 H).
(Step 2)
(2–1) Preparation of allyl (1S, 5R, 6S)-2-[(1R)-1-hydroxy-2-methylpropyl]-6-[(1R)-1-hydroxyethyl]-1-methyl-2-carbapenem-3-carboxylate 1.88 g of allyl (1S, 5R, 6S)-2-[(1R)-1-hydroxy-2-methylpropyl]-6-[(1R)-1-triethylsilyloxyethyl]-1-methyl-2-carbapenem-3-carboxylate prepared in (Step 1) was dissolved in a mixture of THF 60 ml and H$_2$O 60 ml. 12.3 ml of 1M HCl was added thereto while cooling in an ice bath and the mixture was stirred at 0° C. for 1 hour. The reaction mixture was neutralized with an aqueous saturated sodium hydrogencarbonate solution and extracted with ethyl acetate to obtain an organic layer. The organic layer was washed successively with water and an aqueous saturated sodium hydrogencarbonate solution and then dried. The residue was concentrated under a reduced pressure to remove the solvent and the residue was purified with a column chromatograph using hexane/ethyl acetate as an eluent to obtain 870 mg of the title compound.

$^1$ H NMR(CDCl$_3$) δ(ppm)

0.85(d, J=6.7 Hz, 3 H), 1.09(d, J=6.7 Hz, 3 H), 1.27(d, J=6.2 Hz, 3 H), 1.35(d, J=7.3 Hz, 3 H), 1.83–1.93(m, 1 H), 2.32–2.44 (m, 1 H), 3.16–3.24(m, 1 H), 3.25(dd, J=2.8, 6.5 Hz, 1 H), 4.12(dd, J=2.8, 10.0 Hz, 1 H), 4.21–4.31(m, 1 H), 4.68–4.99(m, 3 H), 5.26(dd, J=1.4, 10.3 Hz, 1 H), 5.43(dd, J=1.4, 17.2 Hz, 1 H), 5.90–6.03(m, 1 H).

(2—2) Preparation of potassium (1S, 5R, 6S)-2-[(1R)-1-hydroxy-2-methylpropyl]-6-[(1R)-1-hydroxyethyl]-1-methyl-2-carbapenem-3-carboxylate 0.21 g of allyl (1S, 5R, 6S)-2-[(1R)-1-hydroxy-2-methylpropyl]-6-[(1R)-1-hydroxyethyl]-1-methyl-2-carbapenem-3-carboxylate prepared in (2-1) was dissolved in 12 ml of dry dichloromethane and the reaction flask was wrapped with an aluminum foil. 0.05 g of triphenylphosphine, 0.13 g of potassium 2-ethylhexanoate, 0.12g of 2-ethylhexanoate and 0.60g of tetrakis (triphenylphosphine) palladium(0) were added thereto and the mixture was stirred at room temperature for 2 hours. To the resulting mixture was added 2 ml of water and the organic solvent was removed by evaporation under a reduced pressure. The concentrated aqueous solution thus obtained was washed with ether, purified with reverse-phase medium pressure liquid chromatography(Lobar RP-18 column, mobile phase: 3% acetonitrile in water) and then lyophilized to obtain 0.14 g of the title compound.

$^1$ H NMR(D$_2$O) δ(ppm)

0.61(d, J=6.7 Hz, 3 H), 0.82(d, J=6.7 Hz, 3 H), 1.00(d, J=7.2 Hz, 3 H), 1.11(d, J=6.2 Hz, 3 H), 1.62–1.77(m, 1 H), 2.96–3.08 (m, 1 H), 3.21(dd, J=2.8, 6.5 Hz, 1 H), 3.97(dd, J=2.8, 10.0 Hz, 1 H), 4.01–4.11(m, 1 H), 4.45(d, J=8.9 Hz, 1 H), 4.55(d, J=10.0 Hz, 1 H).

Example 2

Preparation of potassium (1S, 5R, 6S)-2-[(R)-(cyclopropyl) hydroxymethyl]-6-[(1R)-1-hydroxyethyl]-1-methyl-2-carbapenem-3-carboxylate (Step 1)

Preparation of allyl (1S, 5R, 6S)-2-[(R)-(cyclopropyl)-hydroxymethyl]-6-[(1R)-1-triethylsilyloxyethyl]-1-methyl-2-carbapenem-3-carboxylate(Ia) and allyl (1S, 5R, 6S)-2-[(S)-(cyclopropyl)hydroxymethyl]-6-[(1R)-1-triethyl-silyloxyethyl]-1-methyl-2-carbapenem-3-carboxylate(Ib)

0.48 g of lithium pieces was added to 50 ml of dry ether and 2.46 ml of cyclopropyl bromide was added slowly hereto while cooling in an ice bath and the mixture was reacted at room temperature for 2 hours. 8.0 g of allyl (1S, 5R, 6S)-2-formyl-6-[(1R)-1-triethylsilyloxyethyl]-1-methyl-2-carbapenem-3-carboxylate prepared in Preparation Example 1 was dissolved in 120 ml of dry ether and the solution was cooled to –78° C. To the solution was added dropwise the cyclopropyl lithium solution prepared above, and the mixture was stirred at the same temperature for 30 min. To the reaction mixture was added an aqueous saturated ammonium chloride solution and the mixture was extracted with ether to obtain an organic layer. The organic layer was dried and the solvent was removed under a reduced pressure. The residue was separated by silica gel column chromatography using hexane/ethyl acetate(3:1) as an eluent to obtain 4.5 g of title compound (Ia)(R$_f$=0.31) and 2.1 g of title compound (Ib)(R$_f$=0.22).

Compound (Ia)

$^1$ H NMR(CDCl$_3$) δ(ppm)

0.41–0.71(m, 10 H), 0.94(t, J=8.0 Hz, 9 H), 1.05–1.30(m, 7 H), 3.05(d, J=5.0 Hz, 1 H), 3.19–3.39(m, 2 H), 4.00(dd, J=5.0, 9.0 Hz, 1 H), 4.11–4.28(m, 2 H), 4.60–4.85(m, 2 H), 5.25(dd, J=1.4, 10.3 Hz, 1 H), 5.42(dd, J=1.4, 17.2 Hz, 1 H), 5.81–6.02(m, 1 H).

Compound (Ib)

$^1$ H NMR(CDCl$_3$) δ(ppm)

0.35–0.67(m, 10 H), 0.94(t, J=8.0 Hz, 9 H), 1.01–1.29(m, 7 H), 3.02–3.18(m, 1 H), 3.20(dd, J=3.1, 6.5 Hz, 1 H), 3.67(t, 8.6 Hz, 1 H), 4.08–4.30(m, 2 H), 4.48(d, J=9.1 Hz, 1 H), 4.62–4.86 (m, 2 H), 5.25(dd, 1.4, 10.3 Hz, 1 H), 5.44(dd, 1.4, 17.2 Hz, 1 H), 5.83–6.05(m, 1 H).

(Step 2)

(2-1) Preparation of allyl (1S, 5R, 6S)-2-[(R)-(cyclopropyl) hydroxymethyl]-6-[(1R)-1-hydroxyethyl]-1-methyl-2-carbapenem-3-carboxylate The procedure of (Step 2) (2-1) of Example 1 was repeated except that 0.31 g of allyl (1S, 5R, 6S)-2-[(R)-(cyclopropyl)hydroxymethyl]-6-[(1R)-1-triethylsilyloxy ethyl]-1-methyl-2-carbapenem-3-carboxylate was employed as a starting material and the reaction was carried out for 2 hours, to obtain 0.19 g of the title compound.

$^1$ H NMR(CDCl$_3$) δ(ppm)

0.41–0.92(m, 4 H), 1.04–1.39(m, 7 H), 1.62–1.73(6s, 1 H), 3.01(d, J=4.5 Hz, 1 H), 3.26(dd, J=2.8, 6.7 Hz, 1 H), 3.36(dd, J=7.7, 9.3 Hz, 1 H), 4.01–4.32(m, 3 H), 4.61–4.99 (m, 2 H), 5.26(dd, J=1.4, 10.3 Hz, 1 H), 5.43(dd, J=1.4, 17.2 Hz, 1 H), 5.81–6.03(m, 1 H).

(2—2) Preparation of potassium (1S, 5R, 6S)-2-[(R)-(cyclopropyl)hydroxymethyl]-6-[(1R)-1-hydroxyethyl]-1-methyl-2-carbapenem-3-carboxylate The procedure of (Step 2) (2-1) of Example 1 was repeated except that allyl (1S, 5R, 6S)-2-[(R)-(cyclo propyl) hydroxymethyl]-6-[(1R)-1-hydroxy-ethyl]-1-methyl-2-carbapenem-3-carboxylate was employed as a starting material to obtain 0.14 g of the title compound.

$^1$ H NMR(D$_2$O) δ(ppm)

0.02–0.59(m, 4 H), 0.95–1.22(m, 1 H), 1.24(dd, J=7.3, 14.4 Hz, 6 H), 3.27(dd, J=2.5, 6.3 Hz, 1 H), 3.16–3.34(m, 1 H), 3.95(d, J=9.5 Hz, 1 H), 4.03(dd, J=2.5, 9.5 Hz, 1 H), 4.07–4.14(m, 1 H).

Example 3

Preparation of potassium (1S, 5R, 6S)-2-[(R)-(cyclopentyl) hydroxymethyl]-6-[(1R)-1-hydroxyethyl]-1-methyl-2-carbapenem-3-carboxylate (Step 1)

Preparation of allyl (1S, 5R, 6S)-2-[(R)-(cyclopentyl)-hydroxymethyl]-6-[(1R)-1-trimethylsilyloxyethyl]-1-methyl-2-carbapenem-3-carboxylate The procedure of (Step 1) of Example 2 was repeated except that 1.4 ml of 2M cyclopentyl chloride was employed in place of cyclopropyl bromide to obtain 0.802 g of the title compound.

$^1$ H NMR(CDCl$_3$) δ(ppm)

0.60(q, J=8.0 Hz, 6 H), 0.93(t, J=8.0 Hz, 9 H), 1.22(s, 3 H), 1.26(s, 3 H), 1.40–1.73(m, 7 H), 1.79–2.29(m, 2 H), 2.41(d, J=4.1 Hz, 1 H), 3.10–3.22(m, 2 H), 4.09(dd, J=2.9, 9.6 Hz, 1 H), 4.16–4.29(m, 1 H), 4.60–4.86(m, 2 H), 5.24(dd, J=1.4, 10.3 Hz, 1 H), 5.28(s, 1 H), 5.43(dd, J=1.4, 17.2 Hz, 1 H), 5.89–6.23((m, 1 H).

(Step 2)

(2-1) Preparation of allyl (1S, 5R, 6S)-2-[(R)-(cyclopentyl) hydroxymethyl]-6-[(1R)-1-hydroxyethyl]-1-methyl-2-carbapenem-3-carboxylate The procedure of (Step 2) (2–1) of Example 1 was repeated except that 0.516 g of allyl (1S, 5R, 6S)-2-[(R)-(cyclopentyl)hydroxymethyl]-6-[(1R)-1-trimethylsilyloxy ethyl]-1-methyl-2-carbapenem-3-carboxylate was employed as a starting material to obtain 0.257 g of the title compound.

$^1$ H NMR(CDCl$_3$) δ(ppm)

1.31(s, 3 H), 1.34(s, 3 H), 1.41–1.88(m, 8 H), 2.01–2.40 (m, 1 H), 2.23(d, J=4.7 Hz, 1 H), 3.07(d, J=5.0 Hz, 1 H), 3.79(dd, J=1.5, 6.5 Hz, 1 H), 4.14–4.23(m, 1 H), 4.58–4.82 (m, 1 H), 5.01(dd, J=5.0, 8.0 Hz, 1 H), 5.24(dd, J=1.4, 10.3 Hz, 1 H), 5.38(dd, J=1.4, 17.2 Hz, 1 H), 5.56(d, J=1.5 Hz, 1 H), 5.82–6.25(m, 1 H).

(2—2) Preparation of potassium (1S, 5R, 6S)-2-[(R)-(cyclopentyl)hydroxymethyl]-6-[(1R)-1-hydroxyethyl]-1-methyl-2-carbapenem-3-carboxylate The procedure of (Step 2) (2—2) of Example 1 was repeated except that 0.257 g of allyl (1S, 5R, 6S)-2-[(R)-(cyclopentyl)hydroxymethyl]-6-[(1R)-1-hydroxyethyl]-1-methyl-2-carbapenem-3-carboxylate was employed as a starting material to obtain 0.151 g of the title compound.

$^1$ H NMR(D$_2$O) δ(ppm)

1.11(s, 3 H), 1.14(s, 3 H), 1.21–1.68(m, 8 H), 1.81–2.20 (m, 1 H), 2.03(d, J=4.7 Hz, 1 H), 2.87(d, J=5.0 Hz, 1 H), 3.59(dd, J=1.5, 6.5 Hz, 1 H), 3.94–4.03(m, 1 H), 4.38–4.62 (m, 1 H), 4.81(dd, J=5.0, 8.0 Hz, 1 H).

Example 4

Preparation of potassium (1S, 5R, 6S)-2-[(R)-(1,3-thiazolyl) hydroxymethyl]-6-[(1R)-1-hydroxyethyl]-1-methyl-2-carbapenem-3-carboxylate (Step 1) Preparation of allyl (1S, 5R, 6S)-2-[(R)-(1,3-thiazolyl)hydroxymethyl]-6-[(1R)-1-triethylsilyloxy-ethyl]-1-methyl-2-carbapenem-3-carboxylate 0.6 g of thiazole was dissolved in 25 ml of dry THF and cooled to −78° C. 4.4 ml of n-butyl lithium(1.6M hexane solution) was added dropwise thereto and the mixture was stirred for 20 min. 20 ml of a THF solution containing 2.5 g allyl (1S, 5R, 6S)-2-formyl-6-[(1R)-1-triethylsilyloxy ethyl]-1-methyl-2-carbapenem-3-carboxylate prepared in Preparation Example 1 was added slowly thereto at the same temperature. The mixture was stirred at the same temperature for 1 hour. To the reaction mixture was added an aqueous saturated ammonium chloride solution and THF was removed under a reduced pressure. The mixture was extracted with 200 ml of ethyl acetate to obtain an organic layer. The organic layer was dried and the solvent was evaporated under a reduced pressure. The residue was purified by column chromatography to obtain 1.2 g of the title compound.

$^1$ H NMR(CDCl$_3$) δ(ppm)

0.60(q, J=8.0 Hz, 6 H), 0.95(t, J=8.0 Hz, 9 H), 1.20(d, J=7.3 Hz, 3 H), 1.40(d, J=6.6 Hz, 3 H), 1.60(6s, 1 H), 1.75(d, J=5.0 Hz, 1 H), 3.10–3.23(m, 2 H), 4.13–4.22(m, 3 H), 4.70–4.90(m, 2 H), 5.30(dd, J=1.4, 10.3 Hz, 1 H), 5.50(dd, J=1.4, 17.2 Hz, 1 H), 5.90–6.10(m, 1 H), 6.32(d, J=5.0 Hz, 1 H), 7.32(d, J=3.3 Hz, 1 H), 7.77(d, J=3.3 Hz, 1 H).

(Step 2)

(2-1) Preparation of allyl (1S, 5R, 6S)-2-[(R)-(1,3-thiazolyl) hydroxymethyl]-6-[(1R)-1-hydroxyethyl]-1-methyl-2-carbapenem-3-carboxylate The procedure of (Step 2) (2-1) of Example 1 was repeated except that 0.13 g of allyl (1S, 5R, 6S)-2-[(R)-(1, 3-thiazolyl)hydroxymethyl]-6-[(1R)-1-triethylsilyloxy ethyl]-1-ethyl-2-carbapenem-3-carboxylate prepared in (Step 1) was employed as a starting material to obtain 55 mg of the title compound.

$^1$ H NMR(CDCl$_3$) δ(ppm) 1.(11(d, J7.3 Hz$_1$ 3 H), 1.32(d, J=6. 1 Hz, 3 H), 1.74(d, J=5S.0 Hz, 1 H), 3.14–3.34(m, 2 H), 4.19–4.34(m, 3 H), 4.71–4.94(m, 2 H), S.31(dd, J=1.4, 10.3 Hz, 1 H), 5.49 (dd, J=1.4, 17.2 Hz, 1 H), 5.91–6.10(m, 1 H), 6.32(d, J=5.0 Hz, 1 H), 7.38(d, J=3.3 Hz, 1 H), 7.80(d, J=3.3 Hz, 1 H). (2—2) Preparation of potassium (1S, 5R, 6S)-2-[(R)-(1,3-thiazolyl)hydroxymethyl]-6-[(1R)-1-hydroxyethyl]-1-methyl-2-carbapenem-3-carboxylate The procedure of (Step 2) (2—2) of Example 1 was repeated except that 30 mg of allyl (1S, 5R, 6S)-2-[(R)-(1, 3-thiazolyl)hydroxymethyl]-6-[(1R)-1-hydroxyethyl]-1-methyl-2-carbapenem-3-carboxylate prepared in (Step 1) was employed as a starting material to obtain 10.4 mg of the title compound.

$^1$ H NMR(D$_2$O) δ(ppm)

0.91(d, J=7.3 Hz, 3 H), 1.11(d, J=6.1 Hz, 3 H), 1.54(d, J=5.0 Hz, 1 H), 3.04–3.24(m, 2 H), 3.99–4.14(m, 3 H), 6.02(d, J=5.0 Hz, 1 H), 7.18(d, J=3.3 Hz, 1 H), 7.80(d, J=3.3 Hz, 1 H).

Example 5

Preparation of (5-methyl-2-oxo-1,3-dioxolen-4-yl)methyl (1S, 5R, 6S)-2-[(1R)-1-hydroxy-2-methylpropyl]-6-[(1R)-1-hydroxyethyl]-1-methyl-2-carbapenem-3-carboxylate 376 mg of potassium (1S, 5R, 6S)-2-[(1R)-1-hydroxy-2-methylpropyl]-6-[(1R)-1-hydroxyethyl]-1-methyl-2-carbapenem-3-carboxylate prepared in Example 1 was dissolved in 12.60 ml of N,N-dimethylformamide and the temperature was adjusted to 0° C. To the mixture was added 0.22 ml of 4-bromomethyl-5-methyl-2-oxo-1,3-dioxolene was added slowly thereto. The resulting mixture was stirred at the same temperature for 30 min. The reaction mixture was diluted with 40 ml of ethyl acetate and the organic layer was washed with a small amount of water and then with a saturated NaCl solution. The residue was dried over anhydrous magnesium sulfate and purified by column chromatography using hexane-ethyl acetate(1:1) as an eluent to obtain 0.14 g of the title compound.

$^1$ H NMR(CDCl$_3$) δ(ppm)

0.83(d, J=7.0 Hz, 3 H), 1.03(d, J=6.5 Hz, 3 H), 1.25(d, J=7.3 Hz, 3 H), 1.32(d, J=6.3 Hz, 3 H), 1.78–1.91(m, 2 H), 2.18(s, 3 H), 2.22(s, 1 H), 3.10–3.31(m, 1 H), 3.23(dd, J=2.6, 6.6 Hz, 1 H), 4.14(dd, J=2.7, 9.8 Hz, 1 H), 4.15–4.28(m, 1 H), 4.72(dd, J=4.8, 8.4 Hz, 1 H), 4.98(s, 2 H).

Example 6

Preparation of (5-methyl-2-oxo-1,3-dioxolen-4-yl)methyl (1S, 5R, 6S)-2-[(R)-(cyclopropyl)hydroxymethyl]-6-[(1R)-1-hydroxyethyl]-1-methyl-2-carbapenem-3-carboxylate The procedure of Example 5 was repeated except that 0.15 g of potassium (1S, 5R, 6S)-2-[(R)-(cyclopropyl)-hydroxymethyl]-6-[(1R)-1-hydroxyethyl]-1-methyl-2-carbapenem-3-carboxylate prepared in Example 2 was employed as a starting material to obtain 0.85 g of the title compound.

$^1$ H NMR(CDCl$_3$) δ(ppm)

0.13–0.27(m, 1 H), 0.42–0.72(m, 3 H), 0.84(d, J=3.0 Hz, 1 H), 1.25(d, J=7.2 Hz, 3 H), 1.32(d, J=6.4 Hz, 3 H), 1.75–1.85(m, 1 H), 2.17(s, 3 H), 2.71(6s, 1 H), 3.26(dd, J=2.9, 6.4 Hz, 1 H), 3.30–3.48(m, 3 H), 4.10–4.32(m, 3 H), 4.98(d, J=4.2 Hz, 2 H).

Example 7

Preparation of (5-methyl-2-oxo-1,3-dioxolen-4-yl)methyl (1S, 5R, 6S)-2-[(R)-(cyclopentyl)hydroxymethyl]-6-[(1R)-1-hydroxyethyl]-1-methyl-2-carbapenem-3-carboxylate The procedure of Example 5 was repeated except that 100 mg of potassium (1S, 5R, 6S)-2-[(R)-(cyclopentyl)hydroxy-methyl]-6-[(1R)-1-hydroxyethyl]-1-methyl-2-carbapenem-3-carboxylate prepared in Example 3 was employed as a starting material to obtain 75 mg of the title compound.

¹H NMR(CDCl₃) δ(ppm)
1.18–1.38(m, 6 H), 1.45–1.73(m, 9 H), 1.83–1.95(m, 1 H), 2.18(s, 3 H), 3.17–3.34(m, 2 H), 4.10–4.28(m, 2 H), 4.74(dd, J=4.6, 8.8 Hz, 1 H), 5.00(s, 2 H).

Example 8
Preparation of cyclohexyloxycarbonyloxy-1-ethyl (1S, 5R, 6S)-2-[(1R)-1-hydroxy-2-methylpropyl]-6-[(1R)-1-hydroxyethyl]-1-methyl-2-carbapenem-3-carboxylate 60 mg of potassium (1S, 5R, 6S)-2-[(1R)-1-hydroxy-2-methylpropyl]-6-[(1R)-1-hydroxyethyl]-1-methyl-2-carbapenem-3-carboxylate prepared in Example 1 was dissolved in 1.0 ml of N,N-dimethylformamide and the temperature was adjusted to 0° C. To the mixture was added dropwise 200 mg of 1-iodoethyl cyclohexyl carbonate was added slowly thereto at the same temperature. The resulting mixture was stirred at room temperature for 2 hours. The reaction mixture was diluted with 10 ml of ethyl acetate and then washed successively with 10% sodium hyposulfite, water and a saturated NaCl solution. The residue was dried over anhydrous magnesium sulfate and purified by column chromatography to obtain 73 mg of the title compound.

¹H NMR(CDCl₃) δ(ppm)
0.83(d, J=6.9 Hz, 3 H), 1.03(d, J=6.6 Hz, 3 H), 1.20–1.39 (m, 9 H), 1.45–1.74(m, 10 H), 1.82–1.99(m, 1 H), 3.11–3.29 (m, 2 H), 4.14(dd, J=2.8, 9.8 Hz, 1 H), 4.13–4.29(m, 1 H), 4.55–4.75(m, 2 H), 6.80–6.95(m, 1 H).

Example 9
Preparation of isopropyloxycarbonyloxy-1-ethyl (1S, 5R, 6S)-2-[(1R)-1-hydroxy-2-methylpropyl]-6-[(1R)-1-hydroxyethyl]-1-methyl-2-carbapenem-3-carboxylate 100 mg of potassium (1S, 5R, 6S)-2-[(1R)-1-hydroxy-2-methylpropyl]-6-[(1R)-1-hydroxyethyl]-1-methyl-2-carbapenem-3-carboxylate prepared in Example 1 was dissolved in 1.50 ml of N,N-dimethylformamide and the reaction temperature was adjusted to 0° C. To the mixture was added slowly 135 mg of 1-iodoethyl isopropyl carbonate and the resulting mixture was stirred at the same temperature for 30 min. The reaction mixture was diluted with 15 ml of ethyl acetate and the organic layer was washed several times with water and then with a saturated NaCl solution. The organic layer was dried over anhydrous magnesium sulfate and the product was purified by column chromatography to obtain 48 mg of the title compound.

¹H NMR(CDCl₃) δ(ppm)
0.83(d, J=6.7 Hz, 3 H), 1.03(d, J=6.6 Hz, 3 H), 1.15–1.37 (m, 9 H), 1.49–1.70(m, 7 H), 1.75–1.93(m, 1 H), 3.10–3.30 (m, 2 H), 4.14(dd, J=2.5, 9.5 Hz, 1 H), 4.13–4.30(m, 1 H), 4.61–4.75(m, 1 H), 4.80–4.98(m, 1 H), 6.80–6.93(m, 1 H).

Example 10
Preparation of pivaloyloxymethyl (1S, 5R, 6S)-2-[(1R)-1-hydroxy-2-methylpropyl]-6-[(1R)-1-hydroxyethyl]-1-methyl-2-carbapenem-3-carboxylate 50 mg of potassium (1S, 5R, 6S)-2-[(1R)-1-hydroxy-2-methylpropyl]-6-[(1R)-1-hydroxyethyl]-1-methyl-2-carbapenem-3-carboxylate prepared in Example 1 was dissolved in 0.5 ml of N,N-dimethylformamide and the temperature was adjusted to 0° C. To the mixture was added slowly 39 mg of potassium carbonate, 48 mg of iodomethyl t-butyl carbonate was added thereto and the resulting mixture was stirred at the same temperature for 30 min. The reaction mixture was diluted with 5 ml of ethyl acetate and the organic layer was washed several times with water and then with a saturated NaCl solution. The solution was dried over anhydrous magnesium sulfate and the product was purified by column chromatography to obtain 46 mg of the title compound.

¹H NMR(CDCl₃) δ(ppm)
0.81(d, J=6.8 Hz, 3 H), 1.03(d, J=6.5 Hz, 3 H), 1.20(s, 9 H), 1.25(d, J=7.2 Hz, 3 H), 1.32(d, J=6.4 Hz, 3 H), 1.64–1.95 (m, 2 H), 2.07–2.15(m, 1 H), 3.11–3.30(m, 1 H), 3.23(dd, J=4.0, 8.5 Hz, 1 H), 4.15(dd, J=2.9, 9.7 Hz, 1 H), 4.05–4.30 (m, 111), 4.65(dd, J=4.5, 8.8 Hz, 1 H), 5.83(d, J=5.5 Hz, 1 H), 5.95(d, J=5.5 Hz, 1 H).

Test Example 1

Test of Antibacterial Activities

The antibacterial activities of the β-methylcarbapenem compounds of the present invention prepared in the above Examples were determined in accordance with the agar plate dilution method(Hoechst 345). Specifically, about $10^7$ CFU/ml of test bacteria(Hoechst standard strains) was inoculated to a Muller-Hinton agar medium containing serial double dilutions of the test compounds, i.e., compounds prepared in Examples 1 to 3, and incubated at 37° C. for 18 hours. Tribactam(EP 416953) and SUN-5555(Santory Co., Japan) were employed as control materials for carbapenem and penem, respectively. When the incubation was completed, the minimum inhibitory concentration of each test compounds was determined. The result is shown in Table I.

TABLE I

| Strains Compounds | Example 1 | Example 2 | Example 3 | Tribactam | SUN-5555 |
|---|---|---|---|---|---|
| S. pyogenes 308A | 0.013 | 0.007 | 0.004 | 0.013 | 0.013 |
| S. pyogenes 77A | 0.013 | 0.007 | 0.007 | 0.007 | 0.007 |
| S. faecium MD 8b | 3.125 | 0.781 | 0.781 | 1.563 | 6.250 |
| S. aureus SG 511 | 0.098 | 0.049 | 0.098 | 0.098 | 0.098 |
| S. aureus 285 | 0.098 | 0.049 | 0.098 | 0.049 | 0.098 |
| S. aureus 503 | 0.098 | 0.049 | 0.098 | 0.049 | 0.098 |
| E. coli 078 | 0.049 | 0.098 | 0.195 | 0.049 | 0.195 |
| E. coli DC 0 | 0.195 | 0.098 | 1.563 | 0.781 | 0.781 |
| E. coli DC 2 | 0.391 | 0.195 | 0.781 | 0.098 | 0.391 |
| E. coli TEM | 0.195 | 0.098 | 0.391 | 0.391 | 0.391 |
| E. coli 1507 E | 0.049 | 0.049 | 0.098 | 0.195 | 0.195 |
| P. aeruginosa 9027 | >100 | 100.0 | >100.0 | 100.0 | >100.0 |

TABLE I-continued

| Strains Compounds | Example 1 | Example 2 | Example 3 | Tribactam | SUN-5555 |
|---|---|---|---|---|---|
| P. aeruginosa 1592 E | >100 | 100.0 | >100.0 | 100.0 | >100.0 |
| P. aeruginosa 1771 | 100 | 100.0 | >100.0 | 50.0 | >100.0 |
| P. aeruginosa 1771 M | 0.781 | 1.563 | 1.563 | 0.391 | 3.125 |
| S. typhimurium | 0.098 | 0.098 | 0.098 | 0.195 | 0.195 |
| K. oxytoca 1082 E | 1.563 | 0.781 | 1.563 | 1.563 | 0.391 |
| K. aerogenes 1522 E | 0.391 | 0.195 | 0.781 | 0.391 | 0.391 |
| E. cloacae P 99 | 0.781 | 0.781 | 6.250 | 3.125 | 1.563 |
| E. cloacae 1321 E | 0.098 | 0.098 | 0.391 | 0.098 | 0.391 |

As can be seen from Table I, the 3-methylcarbapenem compounds of the present invention exhibit superior antibacterial activities over the controls, Tribactam and SUN-5555. In particular, they show excellent antibacterial activities against *Streptococcus faecium, Klebsiella aerogenes* and *Enterobacter cloacae*.

Test Example 2

In vivo Antibacterial Activity and Pharmacological Activity

The in vivo antibacterial activities and pharmacological activities of the β-methylcarbapenem compounds of the present invention were tested as follows. Specifically, 4 to 5 week-old I.C.R. mouse, each weighing 22 to 25 g and infected with *Streptococcus pyogenes* 77A, were administered per os with the solutions of the compounds of Examples 5 and 9 dissolved in 10% DMSO, at a dosage of 40 mg/kg body weight. The bioavailability indices, e.g., $C_{max}$, $T_{max}$, $t_{1/2}$, AUC and p.o./s.c. were determined in accordance with one-compartment oral model method(*Drug Metabolism Reviews*, 17, 331–348(1986)). The one-compartment oral model was prepared by curve fitting using Gauss-Newto method and calculation using PKCALC computer program. The result is shown in Table II.

TABLE II

| comp. bioavailability | Ex. 5 | Ex. 9 | Trinem[*1] | SUN-5555 |
|---|---|---|---|---|
| $C_{max}$ (μg/ml) | 8.77 | 10.37 | 7.60 | 2.64 |
| $T_{max}$ (hr) | 0.17 | 0.33 | 0.17 | 0.42 |
| $t_{1/2}$ (hr) | 0.27 | 0.33 | 0.35 | 0.38 |
| AUC(μg/ml) | 3.80 | 6.78 | 5.28 | 2.49 |
| p.o./s.c.[*2] | 32.50 | 32.42 | 19.28 | 22.71 |

[*1] An ester of Tribactam(WO 9203437).
[*2] % of blood concentration of test compounds administered per os relative to that of test compounds administered subcutaneously.

As can be seen from Table II, the β-methylcarbapenem compounds prepared in Examples 5 and 9 of the present invention exhibit superior pharmacokinetics values and p.o. absorption over the controls, Trinem and SUN-5555. Therefore, it can be concluded that the β-methylcarbapenem compounds of the present invention may be effectively used for oral administration.

While the invention has been described with respect to the above specific embodiments, it should be recognized that various modifications and changes may be made to the invention by those skilled in the art which also fall within the scope of the invention as defined by the appended claims.

What is claimed is:

1. A β-methylcarbapenem compound of formula (I), a salt or an ester thereof:

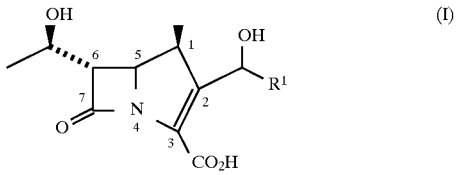

wherein:

$R^1$ is a $C_{1-6}$ alkyl, $C_{2-6}$ alkenyl, cycloalkyl, aryl or thiazolyl group.

2. The 3-methylcarbapenem compound of claim 1, wherein $R^1$ is an isopropyl, t-butyl, cyclopropyl, or cyclopentyl group.

3. The β-methylcarbapenem compound of claim 1, which is selected from the group consisting of:

(1S, 5R, 6S)-2-[(1R)-1-hydroxy-2-methylpropyl]-6-[(1R)-1-hydroxyethyl]-1-methyl-2-carbapenem-3-carboxylic acid;

(1S, 5R, 6S)-2-[(1S)-1-hydroxy-2-methylpropyl]-6-[(1R)-1-hydroxyethyl]-1-methyl-2-carbapenem-3-carboxylic acid;

(1S, 5R, 6S)-2-[(R)-(cyclopropyl)hydroxymethyl]-6-[(1R)-1-hydroxyethyl]-1-methyl-2-carbapenem-3-carboxylic acid;

(1S, 5R, 6S)-2-[(S)-(cyclopropyl)hydroxymethyl]-6-[(1R)-1-hydroxyethyl]-1-methyl-2-carbapenem-3-carboxylic acid;

(1S, 5R, 6S)-2-[(R)-(cyclopentyl)hydroxymethyl]-6-[(1R)-1-hydroxyethyl]-1-methyl-2-carbapenem-3-carboxylic acid;

(1S, 5R, 6S)-2-[(S)-(cyclopentyl)hydroxymethyl]-6-[(1R)-1-hydroxyethyl]-1-methyl-2-carbapenem-3-carboxylic acid;

(1S, 5R, 6S)-2-[(R)-(1,3-thiazolyl)hydroxymethyl]-6-[(1R)-1-hydroxyethyl]-1-methyl-2-carbapenem-3-carboxylic acid;

(1S, 5R, 6S)-2-[(S)-(1,3-thiazolyl)hydroxymethyl]-6-[(1R)-1-hydroxyethyl]-1-methyl-2-carbapenem-3-carboxylic acid;

(1S, 5R, 6S)-2-[(1R)-1-hydroxy-2,2-dimethylpropyl]-6-[(1R)-1-hydroxyethyl]-1-methyl-2-carbapenem-3-carboxylic acid;

(1S, 5R, 6S)-2-[(1S)-1-hydroxy-2,2-dimethylpropyl]-6-[(1R)-1-hydroxyethyl]-1-methyl-2-carbapenem-3-carboxylic acid;

(1S, 5R, 6S)-2-[(1R)-1-hydroxy-3-methylbutyl]-6-[(1R)-1-hydroxyethyl]-1-methyl-2-carbapenem-3-carboxylic acid;

(1S, 5R, 6S)-2-[(1S)-1-hydroxy-3-methylbutyl]-6-[(1R)-1-hydroxyethyl]-1-methyl-2-carbapenem-3-carboxylic acid;

(1S, 5R, 6S)-2-[(1R)-1-hydroxy-3-buten-1-yl]-6-[(1R)-1-hydroxyethyl]-1-methyl-2-carbapenem-3-carboxylic acid;

(1S, 5R, 6S)-2-[(1S)-1-hydroxy-3-buten-1-yl]-6-[(1R)-1-hydroxyethyl]-1-methyl-2-carbapenem-3-carboxylic acid;

(1S, 5R, 6S)-2-[(R)-(phenyl)hydroxymethyl]-6-[(1R)-1-hydroxyethyl]-1-methyl-2-carbapenem-3-carboxylic acid; and (1S, 5R, 6S)-2-[(S)-(phenyl)hydroxymethyl]-6-[(1R)-1-hydroxyethyl]-1-methyl-2-carbapenem-3-carboxylic acid.

4. The salt of the β-methylcarbapenem compound of claim 1, wherein the carboxyl group is neutralized with an organic or inorganic base.

5. The ester of the β-methylcarbapenem compound of claim 1, wherein the carboxyl group is replaced with $CO_2R^4$, $R^4$ being selected from the group consisting of pivaloyloxyalkyl, alkoxycarbonyloxyalkyl cyclohexyloxycarbonyloxymethyl and alkyldioxolenonealkyl groups.

6. The ester of claim 5, which is selected from the group consisting of:

(5-Methyl-2-oxo-1,3-dioxolen-4-yl)-methyl (1S, 5R, 6S)-2-[(R)-(cyclopropyl)hydroxymethyl]-6-[(1R)-1-hydroxy-ethyl]-1-methyl-2-carbapenem-3-carboxylate;

(5-Methyl-2-oxo-1,3-dioxolen-4-yl)-methyl (1S, 5R, 6S)-2-[(R)-(cyclopentyl)hydroxymethyl]-6-[(1R)-1-hydroxy-ethyl]-1-methyl-2-carbapenem-3-carboxylate;

(5-Methyl-2-oxo-1,3-dioxolen-4-yl)-methyl (1S, 5R, 6S)-2-[(1R)-1-hydroxy-2-methylpropyl]-6-[(1R)-1-hydroxy-ethyl]-1-methyl-2-carbapenem-3-carboxylate;

Cyclohexyloxycarbonyloxy-1-ethyl (1S, 5R, 6S)-2-[(1R)-1-hydroxy-2-methylpropyl]-6-[(1R)-1-hydroxyethyl]-1-methyl-2-carbapenem-3-carboxylate;

Isopropylcarbonyloxy-1-ethyl (1S, 5R, 6S)-2-[(1R)-1-hydroxy-2-methylpropyl]-6-[(1R)-1-hydroxyethyl]-1-methyl-2-carbapenem-3-carboxylate; and Pivaloyloxymethyl (1S, 5R, 6S)-2-[(1R)-1-hydroxy-2-methylpropyl]-6-[(1R)-1-hydroxyethyl]-1-methyl-2-carbapenem-3-carboxylate.

7. An antibacterial composition comprising the β-methylcarbapenem compound of claim 1 together with a pharmaceutically acceptable carrier or excipient.

* * * * *

UNITED STATES PATENT AND TRADEMARK OFFICE
CERTIFICATE OF CORRECTION

PATENT NO. : 5,869,477
DATED : February 9, 1999
INVENTOR(S) : Cheol-Hae Lee, et al It is certified that error appears in the above-identified patent and that said Letters Patent is hereby corrected as shown below:

On the title page,

[73]   Assignee:   Korea Research Institute of Chemical Technology, Daejeon, Rep of Korea

[30] Foreign Application Priority Data

Dec. 4, 1996   [KR]   Rep. of Korea   95-46454

Signed and Sealed this

Twenty-second Day of June, 1999

Attest:

Q. TODD DICKINSON

*Attesting Officer*   *Acting Commissioner of Patents and Trademarks*